United States Patent [19]

Powers et al.

[11] Patent Number: 5,089,633

[45] Date of Patent: Feb. 18, 1992

[54] SUBSTITUTED ISOCOUMARINS

[75] Inventors: James C. Powers, Atlanta; Chih-Min Kam, Roswell, both of Ga.; Josef Oleksyszyn, Westminster, Colo.; J. A. Glinski, New Fairfield, Conn.; M. A. Hernandez, Norcross, Ga.

[73] Assignee: Georgia Tech Research Corporation, Atlanta, Ga.

[21] Appl. No.: 516,786

[22] Filed: Apr. 30, 1990

Related U.S. Application Data

[63] Continuation-in-part of Ser. No. 215,994, Jul. 7, 1988, abandoned, and a continuation-in-part of Ser. No. 374,980, Jul. 3, 1989, Pat. No. 4,954,519.

[51] Int. Cl.$^5$ .......................................... C07D 31/365
[52] U.S. Cl. .................................. 549/285; 548/303; 548/463; 548/495; 548/518; 548/336; 548/344; 548/525; 530/329; 530/330; 530/331
[58] Field of Search ........................................ 549/285

[56] References Cited

U.S. PATENT DOCUMENTS 4,596,822 6/1986 Powers et al. ...................... 514/459

OTHER PUBLICATIONS

Kiyoaki et al., CA 88:169969a.
Takuya et al., CA 104:88435v.

Primary Examiner—Jane T. Fan
Attorney, Agent, or Firm—Hurt, Richardson, Garner, Todd & Cadenhead

[57] ABSTRACT

Substituted isocoumarins, their use in inhibiting serine proteases with chymotrypsin-like and elastase-like specificity and their roles as anti-inflammatory agents.

15 Claims, No Drawings

SUBSTITUTED ISOCOUMARINS

STATEMENT OF GOVERNMENT INTEREST

This invention was made with government support under Contract No. HL34035 and HL29307 awarded by the National Institutes of Health, National Heart, Lung and Blood Institute. The government has certain rights in the invention.

This is a continuation-in-part of copending applications Ser. Nos. 215,994 filed on July 7, 1988 now abandoned, 374,980 filed on July 3, 1989 now U.S. Pat. No. 4,954,519, issued Sep. 4, 1990.

BACKGROUND OF THE INVENTION

1. Field of the Invention

This invention relates to a novel class of heterocyclic compounds useful for selectively inhibiting chymotrypsin-like enzymes, selectively inhibiting elastase or for generally inhibiting serine proteases of all classes. This invention also relates to a method of treating inflammation in patients using the novel compounds of the present invention. We have found that isocoumarins substituted with hydrophobic groups are potent inhibitors of chymases and elastase, therefore they are useful as anti-inflammatory agents.

2. Description of the Related Art

Serine proteases play critical roles in several physiological processes such as digestion, blood coagulation, complement activation, fibrinolysis, viral infection, fertilization, and reproduction. Serine proteases are not only a physiological necessity, but also a potential hazard if they are not controlled. Uncontrolled proteolysis by elastases may cause pancreatitis, emphysema, rheumatoid arthritis, bronchial inflammation and adult respiratory distress syndrome. Human polymorphonuclear leukocyte elastase may also be involved in blistering. Accordingly, specific and selective inhibitors of these proteases should be potent anti-inflammatory agents useful in the treatment of protease-related diseases (Powers and Harper, in Proteinase Inhibitors, Barrett and Salvesen, eds., Elsevier, 1986, pp 55-152, incorporated herein by reference). In vitro proteolysis by chymotrypsin or the elastase family is a serious problem in the production, purification, isolation, transport or storage of peptides and proteins.

Anti-inflammatory agents were used to treat elastases-associated inflammation including rheumatoid arthritis and emphysema. Although the naturally occurring protease inhibitor, $\alpha$1-protease inhibitor ($\alpha$1-PI) has been used to treat patients with emphysema, this inhibitor is not widely used clinically due to the high dosage needed for the treatment and difficulty of producing large quantities. Therefore small molecular weight elastase inhibitors are needed for therapy.

SUMMARY OF THE INVENTION

It is an object of this invention to find a novel group of specific inhibitors for elastase, chymotrypsin and other serine proteases of similar substrate specificity and for serine proteases in general. Inhibitors are compounds that reduce or eliminate the catalytic activity of the enzyme. Trypsin and trypsin-like enzymes normally cleave peptide bonds in proteins and peptides where the amino acid residue on the carbonyl side of the split bond ($P_1$ residue) is Lys or Arg. Elastase and elastase-like enzymes, on the other hand, cleave peptide bonds where the $P_1$ amino acid is Ala, Val, Ser, Leu and other similar amino acids. Chymotrypsin and chymotrypsin-like enzymes hydrolyze peptide bonds where $P_1$ amino acid is Trp, Tyr, Phe, Met, Leu or other amino acid residues which contain aromatic or large alkyl side chains. All of the above enzymes have extensive secondary specificity and recognize amino acid residues removed from the $P_1$ residue.

It is an object of this invention to discover new protease inhibitors, especially elastase inhibitors, and chymase inhibitors. These inhibitors are useful for controlling tissue damage and various inflammatory conditions mediated by proteases particularly elastases. The inhibitors of this invention would also be useful for controlling hormone processing by serine proteases and for treating diseases related to tryptases and chymases such as inflammation and skin blistering.

It is a further object of this invention to find a novel group of specific inhibitors useful in vitro for inhibiting trypsin, elastase, chymotrypsin and other serine proteases of similar specificity and for inhibiting serine proteases in general. Such inhibitors could be used to identify new proteolytic enzymes encountered in research. They could also be used in research and industrially to prevent undesired proteolysis that occurs during the production, isolation, purification, transport and storage of valuable peptides and proteins. Such proteolysis often destroys or alters the activity and/or function of the peptides and proteins. Uses would include the addition of the inhibitors to antibodies, enzymes, plasma proteins, tissue extracts or other proteins and peptides which are widely sold for use in clinical analyses, biomedical research, and for many other reasons. For some uses a specific inhibitor would be desirable, while in other cases, an inhibitor with general specificity would be preferred.

DETAILED DESCRIPTION OF THE INVENTION

Isocoumarins substituted with hydrophobic groups have been found to be excellent inhibitors of several serine proteases including human leukocyte elastase, porcine pancreatic elastase, bovine chymotrypsin and human leukocyte cathepsin G. These compounds inhibit the serine proteases by reaction with the active site serine to form an acyl enzyme, which in some cases may further react with another active site nucleophile to form an additional covalent bond. These structures may be used in vivo to treat diseases such as emphysema, adult respiratory distress syndrome, rheumatoid arthritis and pancreatitis which result from uncontrolled proteolysis by elastase, chymotrypsin, trypsin and related serine proteases. These inhibitors may be used in vitro to prevent proteolysis which occurs in the process of production, isolation, purification, storage or transport of peptides and proteins. The novel substituted isocoumarin and related heterocyclic compounds have the following structural formula:

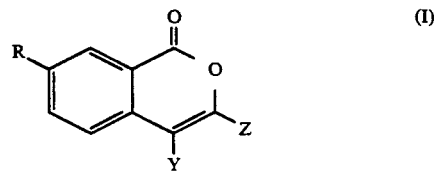

or a pharmaceutically acceptable salt, wherein

Z is methoxy,

R is selected from the group consisting of O=C=N—, S=C=N—, M—NH—, M—AA—NH—, M—AA—AA—NH—, M—O—, M—AA—O, M—AA—AA—O—, wherein M represents $NH_2$—CO—, $NH_2$—CS—, $NH_2$—$SO_2$—, X—NH—CO—, X—NH—CS—, X—NH—$SO_2$—, X—CS—, X—$SO_2$—, X—O—CO—, X—O—CS—, or D—CO—, wherein X represents $C_{1-6}$ alkyl, $C_{1-6}$ fluoroalkyl, $C_{1-6}$ alkyl substituted with K, $C_{1-6}$ fluoroalkyl substituted with K, 9-fluoroenylmethyl, phenyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group, $C_{1-6}$ alkyl with two attached phenyl groups, $C_{1-6}$ alkyl with an attached phenyl group substituted with J, or $C_{1-6}$ alkyl with two attached phenyl groups substituted with J, wherein D represents $C_{1-6}$ fluoroalkyl, $C_{1-6}$ alkyl substituted with K, $C_{1-6}$ fluoroalkyl substituted with K, 9-fluorenylmethyl, phenyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group substituted with J, or $C_{1-6}$ alkyl with two attached phenyl groups substituted with J, wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl—O—CO—, $C_{1-6}$ alkyl—O—CO—NH—, or $C_{1-6}$ alkyl—S—, wherein K represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl—O—CO—, or $C_{1-6}$ alkyl—O—CO—NH, $C_{1-6}$ alkyl—S—, or tosylamino, wherein AA represents alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, phenylglycine, alpha-aminobutyric acid, epsilon-aminocaproic acid, citrulline, hydroxyproline, ornithine or sarcosine, and Y is selected from the group consisting of H, halogen, trifluoromethyl, methyl, OH and methoxy.

Alternately the novel isocoumarin and related heterocyclic compound are represented by structure (I) where, Z is ethoxy, wherein R is selected from the group consisting of O=C=N—, S=C=N—, M—NH—, M—AA—NH—, M—AA—AA—NH—, M—O—, M—AA—O, M—AA—AA—O—, wherein M represents $NH_2$—CS—, $NH_2$—$SO_2$—, L—NH—CO—, X—NH—CS—, X—NH—$SO_2$—, X—CO—, X—CS—, X—$SO_2$—, X—O—CO—, or X—O—CS—, wherein L represents $C_{1-6}$ fluoroalkyl, $C_{1-6}$ alkyl substituted with K, $C_{1-6}$ fluoroalkyl substituted with K, 9-fluorenylmethyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group, $C_{1-6}$ alkyl with two attached phenyl groups, $C_{1-6}$ alkyl with an attached phenyl group substituted with J, or $C_{1-6}$ alkyl with two attached phenyl groups substituted with J, wherein X represents $C_{1-6}$ alkyl, $C_{1-6}$ fluoroalkyl, $C_{1-6}$ alkyl substituted with K, $C_{1-6}$ fluoroalkyl substituted with K, 9-fluorenyl, phenyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group, $C_{1-6}$ alkyl with two attached phenyl groups, $C_{1-6}$ alkyl with an attached phenyl group substituted with J, or $C_{1-6}$ alkyl with two attached phenyl groups substituted with J, wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl—O—CO—, $C_{1-6}$ alkyl—O—CO—NH—, or $C_{1-6}$ alkyl—S—, wherein K represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl—O—CO—, or $C_{1-6}$ alkyl—O—CO—NH, $C_{1-6}$ alkyl—S—, or tosylamino, wherein AA represents alanine, valine, leucine, isoleucine, proline, methionine, phenylalanine, tryptophan, Alternately the novel isocoumarin and related heterocyclic compound are represented by structure (I) where, Z is selected from the group consisting of propoxy, $C_{1-6}$ alkoxy with a phenyl group attached to the $C_{1-6}$ alkoxy group, $C_{1-6}$ alkyl with a phenyl group attached to the $C_{1-6}$ alkyl, $C_{1-6}$ alkoxy with an attached phenyl group substituted with J, $C_{1-6}$ alkyl with an attached phenyl group substituted with J, glycine, serine, threonine, cysteine, tyrosine, asparagine, glutamine, aspartic acid, glutamic acid, lysine, arginine, histidine, beta-alanine, norleucine, norvaline, phenylglycine, alpha-aminobutyric acid, epsilon-aminocaproic acid, citrulline, hydroxyproline, ornithine or sarcosine, and Y is selected from the group consisting of H, halogen, trifluoromethyl, methyl, OH and methoxy.

Alternately the novel isocoumarin and related heterocyclic compound are represented by structure (I) where, wherein Z is selected from the group consisting of $C_{1-6}$ alkoxy with a halogen attached to the alkoxy group, $C_{1-6}$ alkyl with a halogen attached to the alkyl group, $C_{1-6}$ alkoxy with an attached $C_{1-6}$ alkoxy group substituted with Q, wherein Q represents H, or $C_{1-6}$ alkoxy, R is selected from the group consisting of OH, $NH_2$, $NO_2$, O=C=N—, S=C=N—, AA—NH—, AA—AA—NH, AA—O—, AA—AA—O—, M—NH—, M—AA—NH—, M—AA—AA—NH—, M—O—, M—AA—O, M—AA—AA—O—, wherein AA represents alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, phenylglycine, alpha-aminobutyric acid, epsilon-aminocaproic acid, citrulline, hydroxyproline, ornithine or sarcosine, wherein M represents $NH_2$—CO—, $NH_2$—CS—, $NH_2$—CS—, $NH_2$—$SO_2$—, X—NH—CO—, X—NH—CS—, X—NH—$SO_2$—, X—CO—, X—CS—, X—$SO_2$—, X—O—CO—, or X—O—CS—, wherein X represents $C_{1-6}$ alkyl, $C_{1-6}$ fluoroalkyl, $C_{1-6}$ alkyl substituted with K, $C_{1-6}$ fluoroalkyl substituted with K, phenyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group, $C_{1-6}$ alkyl with two attached phenyl groups, $C_{1-6}$ alkyl with an attached phenyl group substituted with J, or $C_{1-6}$ alkyl with two attached phenyl groups substituted with J, wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl—O—CO—, $C_{1-6}$ alkyl—O—CO—NH—, or $C_{1-6}$ alkyl—S—, wherein K represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl—O—CO—, or $C_{1-6}$ alkyl—O—CO—NH—, $C_{1-6}$ alkyl—S—, or tosylamino, and Y is selected from the group consisting of H, halogen, trifluoromethyl, methyl, OH and methoxy.

Alternately the novel isocoumarin and related heterocyclic compounds are represented by structure (I) where, Z is selected from the group consisting of H, halogen, $C_{1-6}$ alkyl, $C_{1-6}$ fluorinated alkyl, $C_{1-6}$ alkyl substituted with K, $C_{1-6}$ fluorinated alkyl substituted with K, $C_{1-6}$ alkoxy, $C_{1-6}$ fluorinated alkoxy, $C_{1-6}$ alkoxy substituted with K, $C_{1-6}$ fluorinated alkoxy substituted with K, $C_{1-6}$ alkyl with a phenyl group attached to the alkyl group, $C_{1-6}$ alkoxy with a phenyl group attached to the alkoxy group, $C_{1-6}$ alkyl with an attached phenyl group substituted with J, $C_{1-6}$ alkyl with an attached phenyl group disubstituted with J, $C_{1-6}$ alkoxy with an attached phenyl group substituted with J, $C_{1-6}$ alkoxy with an attached phenyl group disubstituted with J, wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl—O—CO—, $C_{1-6}$ alkyl—O—CO—NH—, or $C_{1-6}$ alkyl—S—, wherein K represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl—O—CO—, or $C_{1-6}$ alkyl—O—CO—NH—, $C_{1-6}$ alkyl—S—, or tosylamino, R is biotin-spacer-T, wherein T represents —NH—, —O—, or —S—, wherein spacer represents —[NH—$(CH_2)_n$—CO]$_n$—, —[NH—$(CH_2)_n$—NH—CO]$_n$—, —[NH—$C_6H_4$—CO]$_n$—, —[NH—$C_6H_4$—NH—CO]$_n$—, —NH—$(CH_2)_n$—CO—NH—$(CH_2)_n$—NH—CO—, —NH—$(CH_2)_n$—CO—NH—$(CH_2)_3$—NH—$(CH_2)_3$—NH—CO—$CH_2CH_2$—CO—, or —(AA)$_n$—, where n=1-6.

wherein AA represents alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, phenylglycine, alpha-aminobutyric acid, epsilon-aminocaproic acid, citrulline, hydroxyproline, ornithine or sarcosine, Y is selected from the group consisting of H, halogen, trifluoromethyl, methyl, OH and methoxy.

The compounds of Formula (I) can also contain one or more substituents at position B as shown in the following structure:

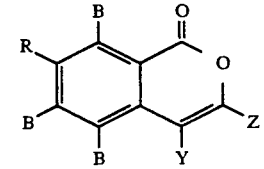

wherein electronegative substituents such as $NO_2$, CN, Cl, COOR, and COOH will increase the reactivity of the isocoumarin, and electropositive substituents such as $NH_2$, OH, alkoxy, thioalkyl, alkyl, alkylamino, and dialkylamino will increase its stability. Neutral substituents could also increase the stability of acyl enzyme and improve the effectiveness of the inhibitors.

Other substituted isocoumarins have been prepared earlier for other purposes (illustrative examples: 3-chloroisocoumarin, Davies and Poole, J. Chem. Soc., pp 1616-1629 (1928); 3-chloro and 3,4-dichloroisocoumarin, Milevskaya, Belinskaya, and Yagupol'skii, Zhur. Org. Khim. 9, pp 2145-2149 (1973); 3-methyl and 4-carboxy-3-methylisocoumarin, Tirodkar and Usgaonkar, Ind. J. Chem. 7, pp 1114-1116 (1969); 7-nitro and 7-aminoisocoumarin, Choksey and Usgaonkar, Ind. J. Chem. 14B, pp 596-598 (1976), the preceding articles are incorporated herein by reference).

A number of other substituted isocoumarins have been prepared recently for inhibition of serine proteases (3-chloroisocoumarin, Harper, Hemmi, and Powers, J. Am. Chem. Soc. 105, pp 6518-6520 (1983); 3,4-dichloroisocoumarin, Harper, Hemmi, and Powers, Biochemistry 24, pp 1831-1841 (1985); 3-alkoxy-7-amino-4-chloroisocoumarin, Harper and Powers, J. Am. Chem. Soc. 106, pp 7618-7619 (1984), Harper and Powers, Biochemistry 24, 7200–7213 (1983); substituted isocoumarins with basic groups (aminoalkoxy, guanidino or isothiureidoalkoxy), Kam, Fujikawa and Powers, Biochemistry 27, pp 2547–2557 (1988); 7-substituted 3-alkoxy-4-chloroisocoumarins, Powers, Kam, Narasimhan, Oleksyszyn, Hernandez and Ueda, J. Cell Biochem. 39, pp 33–46 (1989), Powers, Oleksyszyn, Narasimhan, Kam, Radhakrishnan and Meyer, Jr. Biochemistry 29, 3108–3118 (1990), the preceding articles are incorporated herein by reference; Powers and Harper, U.S. Pat. No. 4,596,822; Powers and Kam, U.S. Pat. No. 4,845,242 which are also incorporated by reference).

The following compounds are representative of the invention:

7-isocyanato-4-chloro-3-methoxyisocoumarin
7-ethoxycarbonylamino-4-chloro-3-methoxyisocoumarin
7-phenoxycarbonylamino-4-chloro-3-methoxyisocoumarin
7-benzyloxycarbonylamino-4-chloro-3-methoxyisocoumarin
7-carbamoylamino-4-chloro-3-methoxyisocoumarin
7-methylcarbamoylamino-4-chloro-3-methoxyisocoumarin
7-ethylcarbamoylamino-4-chloro-3-methoxyisocoumarin
7-isopropylcarbamoylamino-4-chloro-3-methoxyisocoumarin
7-t-butylcarbamoylamino-4-chloro-3-methoxyisocoumarin
7-phenylcarbamoylamino-4-chloro-3-methoxyisocoumarin
7-(N-benzyl-N-phenylethylcarbamoyl)amino-4-chloro-3-methoxyisocoumarin
7-heptafluorobutyroylamino-4-chloro-3-methoxyisocoumarin
7-(9-fluorenylmethoxycarbonyl)amino-4-chloro-3-methoxyisocoumarin
7-(N-tosyl-α-phenylglycyl)amino-4-chloro-3-methoxyisocoumarin
7-(o-phthalyl)amino-4-chloro-3-methoxyisocoumarin
7-(o-methoxyphthalyl)amino-4-chloro-3-methoxyisocoumarin
7-methoxysuccinylamino-4-chloro-3-methoxyisocoumarin
7-methoxyglutarylamino-4-chloro-3-methoxyisocoumarin
7-(3-phenylglutaryl)amino-4-chloro-3-methoxyisocoumarin
7-(m-methoxycarbonylaminobenzoyl)amino-4-chloro-3-methoxyisocoumarin
7-ethoxycarbonylamino-4-chloro-3-ethoxyisocoumarin
7-ethylthiocarbamoylamino-4-chloro-3-ethoxyisocoumarin
7-phenylthiocarbamoylamino-4-chloro-3-ethoxyisocoumarin
7-dihydrocinnamoylamino-4-chloro-3-propyloxyisocoumarin
7-ethoxycarbonylamino-4-chloro-3-propyloxyisocoumarin
7-ethylcarbamoylamino-4-chloro-3-propyloxyisocoumarin
7-phenylcarbamoylamino-4-chloro-3-propyloxyisocoumarin
7-phenylthiocarbamoylamino-4-chloro-3-propyloxyisocoumarin
7-benzylthiocarbamoylamino-4-chloro-3-propyloxyisocoumarin
7-(m-nitrobenzoyl)amino-4-chloro-3-propyloxyisocoumarin
7-[(2-thiomethyl)acetyl]amino-4-chloro-3-propyloxyisocoumarin
7-(N-t-butyloxycarbonyl-valyl)amino-4-chloro-3-propyloxyisocoumarin
7-biotinylamino-4-chloro-3-propyloxyisocoumarin
7-biotinylamino-4-chloro-3-(2-phenylethoxy)isocoumarin
7-(6-biotinylaminocaproyl)amino-4-chloro-3-ethoxyisocoumarin
7-(6-biotinylaminocaproyl)amino-4-chloro-3-propyloxyisocoumarin
7-(6-biotinylaminocaproyl)amino-4-chloro-3-(2-phenylethoxy)isocoumarin
7-nitro-4-chloro-3-(2-bromoethoxy)isocoumarin
7-amino-4-chloro-3-(2-bromoethoxy)isocoumarin
7-t-butylcarbamoylamino-4-chloro-3-(2-bromoethoxy)isocoumarin
7-isopropylcarbamoylamino-4-chloro-3-(2-bromoethoxy)isocoumarin
7-phenylcarbamoylamino-4-chloro-3-(2-bromoethoxy)isocoumarin
7-benzylcarbamoylamino-4-chloro-3-(2-bromoethoxy)isocoumarin
7-(R-α-methylbenzyl)carbamoylamino-4-chloro-3-(2-bromoethoxy)isocoumarin
7-(S-α-methylbenzyl)carbamoylamino-4-chloro-3-(2-bromoethoxy)isocoumarin
7-naphthylcarbamoylamino-4-chloro-3-(2-bromoethoxy)isocoumarin
7-t-butylacetylamino-4-chloro-3-(2-bromoethoxy)isocoumarin
7-phenylacetylamino-4-chloro-3-(2-bromoethoxy)isocoumarin
7-(N-t-butyloxycarbonyl-D-phenylalanyl)amino-4-chloro-3-(2-bromoethoxy)isocoumarin
7-(N-t-butyloxycarbonyl-L-phenylalanyl)amino-4-chloro-3-(2-bromoethoxy)isocoumarin
7-(N-t-butyloxycarbonyl-L-alanylalanyl)amino-4-chloro-3-(2-bromoethoxy)isocoumarin
7-dansylamino-4-chloro-3-(2-bromoethoxy)isocoumarin
7-phenylthiocarbamoylamino-4-chloro-3-(2-bromoethoxy)isocoumarin
7-(m-carboxyphenyl)thiocarbamoylamino-4-chloro-3-(2-bromoethoxy)isocoumarin
7-(p-carboxyphenyl)thiocarbamoylamino-4-chloro-3-(2-bromoethoxy)isocoumarin
7-nitro-4-chloro-3-(3-bromopropoxy)isocoumarin
7-amino-4-chloro-3-(3-bromopropoxy)isocoumarin
7-phenylcarbamoylamino-4-chloro-3-(3-bromopropoxy)isocoumarin
7-benzylcarbamoylamino-4-chloro-3-(3-bromopropoxy)isocoumarin
7-acetylamino-4-chloro-3-(3-bromopropoxy)isocoumarin
7-phenylacetylamino-4-chloro-3-(3-bromopropoxy)isocoumarin
7-dihydrocinnamoylamino-4-chloro-3-(3-bromopropoxy)isocoumarin
7-(N-t-butyloxycarbonyl-D-phenylalanyl)amino-4-chloro-3-(3-bromopropoxy)isocoumarin
7-(N-t-butyloxycarbonyl-L-phenylalanyl)amino-4-chloro-3-(3-bromopropoxy)isocoumarin
7-nitro-4-chloro-3-(2-bromoisopropoxy)isocoumarin
7-amino-4-chloro-3-(2-bromoisopropoxy)isocoumarin 7-amino-4-chloro-3-(2-methoxy)ethoxyisocoumarin
7-amino-4-chloro-3-[2-(2-methoxyethoxy)ethoxy]isocoumarin It has been found that compounds of Formula (I) have anti-inflammatory activity and can be used to treat and control emphysema, adult respiratory distress syndrome and rheumatoid arthritis as shown in Table I, III, IV and VII by effective inhibition of the proteolytic function of human leukocyte elastase and human cathepsin G. Compounds of Formula (I) are effective in the theraputic use for pancreatitis by inhibiting the proteolytic function of chymotrypsin and pancreatic elastase as shown in Table I, II, III, IV and VII. Compounds of Formula (I) are also effective in the prevention of unnecessary proteolysis caused by chymotrypsin and elastase in the process of purification, transport and storage of peptides and proteins as shown in Table I, II, III, IV and VII by effective inhibition of chymotrypsin and elastase.

Compounds of Formula (I) with a R group consisting of biotinylamino or an alkanoylamino with biotinylamino group attached to alkanoylamino, Y group of Cl, and Z group of phenylethoxy group are effective in the inhibition of rat granule chymase as shown in Table V. The reactivation of inhibited rat granule chymase by these biotin isocoumarins in the presence of hydroxylamine as shown in Table VI is useful in the purification of these enzymes from rat granules by applying the inhibited granules to the avidin beads, where the biotinylated enzymes form tight complex with avidin and retain on the column. Finally the enzyme can be reactivated and eluated out with hydroxylamine solution. The tight complex of biotin-avidin has been used as a powerful tool for purifying proteins. One such an example was shown by Williams et al., J. Biol. Chem. 264, pp 7536–7545 (1989). The biotinylated-$\epsilon$-aminocaproyl-peptide chloromethylketone was used to react with an active protease to form the biotinylated inactivated enzyme which retained on the avidin beads. This procedure allows removal of the protease from enzyme and zymogen mixture.

Although little information is available on the structure of biotin binding site of avidin, the spacer between the biotin and the ligand molecule such as isocoumarin, chloromethyl ketone or insulin is crucial for the binding of biotinylated ligand to avidin. Green et al. (Biochem. J. 125, pp 781–791 (1971)) attempted to determine the depth of the biotin binding site on avidin by studying the effect of chain length of $\omega$-bis(biotinyldiamines) on avidin polymer formation. He concluded that since stable polymers were formed when the chain linking the carboxyl groups of the biotins was 18 Å long, the carboxyl group must lie about 8–9 Å beneath the surface of the avidin molecule. Finn et al. (Biochemistry 23, pp 2554–2558 (1984)) also calculated that the distance between the carboxyl group of dethiobiotin and the N-terminal amino group of the insulin B-chain would be 9.77 Å for dethiobiotinyl-A1-insulin, 18.36 Å for dethiobiotinyl-A2-insulin, and 25.52 Å for dethiobiotinyl-A1-DPA-insulin (A1, A2, and A1-DPA were different chain length of spacer). Thus, any of these ligands should have sufficient space between the dethiobiotinyl and insulin portions to bind normally to avidin. However, only the longest of the three ligands showed the same rate of dissociation from Suc-avidin as dethiobiotin itself. Therefore, spacer arms are required for optimizing the interaction between the biotinylated ligand and the avidin complex.

The biotin-avidin interaction is very useful in many areas such as immunoassays, receptor studies, immunocytochemical staining and protein isolation. In the enzyme immunoassay system, the biotinylated antibody is bound to the immobilized antigen or primary antibody, and avidin can be conjugated with enzymes, fluorochromes, ferritin or colloidal markers. The biotin-avidin interaction can also be used in blotting techniques for detecting proteins. It is very useful in the staining of cellular antigenic determinants. A wide variety of biotinylated primary probes such as monoclonal antibodies, lectins, vitamins, sugars, hormones and lipoproteins have been used. This specific interaction has also been used successfully in the selective retrieval of labelled plasma membrane components (Orr, J. Biol. Chem. 256, pp 761–766 (1981)). Biotinylated protein can be used as probes of protein structure and protein-protein interaction (Billingsley et al. Biotechniques 5, pp 22–31 (1987)).

Inactivation rates of serine proteases by substituted isocoumarins were measured by the incubation method. An aliquot of inhibitor (25 or 50 $\mu$l) in Me$_2$SO was added to a buffered enzyme solution (0.01–2.3 $\mu$M) to initiate the inactivation. Aliquots (50 $\mu$l) were withdrawn at various intervals and the residual enzymatic activity was measured. Me$_2$SO concentration in the reaction mixture was 8–12% (v/v). 0.1M Hepes, 0.5M NaCl, pH 7.5 buffer was utilized for the assays of all serine proteases. The inhibitor concentrations are shown in the Tables I, II, III, IV, V, VI and VII. Peptide nitroanilides with appropriate sequence were used as substrates for various serine proteases. All peptide 4-nitroanilide hydrolysis was measured at 410 nm ($\epsilon_{410} = 8800 M^{-1} cm^{-1}$; Erlanger et al., Arch. Biochem. Biophys. 95, pp 271–278 (1961)). First order inactivation rate constant ($k_{obs}$) were obtained from plots of ln ($v_t/v_o$) vs time, and the correlation coefficients were greater than 0.98.

Table I shows the inactivation rate constants of porcine pancreatic elastase (PPE), human leukocyte elastase (HLE) inhibited by substituted isocoumarins. The inactivation by these inhibitors was less efficient toward PPE than HLE. The structures with R group of o-methoxyphthalylamino or phenylcarbamoylamino, Y group of Cl, and Z group of methoxy are best inhibitors for PPE. The structures with R group of Tosphenylglycylamino or m-methoxycarbonylaminobenzoylamino, Y group of Cl, and Z-group of methoxy are best at inhibiting HLE.

Table II shows the inhibition of PPE by substituted isocoumarins, the structure with R group of phenylthiocarbamylamino, Y group of Cl, and Z-group of ethoxy is the best inhibitor of PPE. Table III shows the inhibition of PPE, HLE, chymotrypsin and cathepsin G by substituted isocoumarins. It is unexpected that all the compounds with Y group of Cl and Z group of propoxy are very potent inhibitors of HLE. The structure with R group of phenylcarbamoylamino, or dihydrocinnamoylamino, Y group of Cl, and Z group of propoxy are the best inhibitors of HLE. However they are poor inhibitors of cathepsin G. The structure with R group of ethoxycarbonylamino, Y group of Cl and Z group of propoxy is a good inhibitor for chymotrypsin.

Table IV shows the inhibition of PPE, HLE, chymotrypsin and cathepsin G by biotin isocoumarin derivatives. The compound with R group of 6-biotinylaminocaproylamino, Y group of Cl and Z group of phenylethoxy is a good inhibitor for chymotrysin.

The structure with R group of 6-biotinylaminocaproylamino, Y group of Cl and Z group of propoxy or ethoxy are the best inhibitors for HLE.

Table V shows the inhibition of rat granule chymase and tryptase by biotin isocoumarin derivatives. The structure with a R group of 6-biotinylaminocaproylamino, Y group of Cl and Z group of phenylethoxy inactivated chymase instantly with 50% inhibition, and also inhibited tryptase very slowly. Table VI shows the reactivation of inhibited chymotrypsin and rat granule chymase by biotin isocoumarins in buffer and in the presence of hydroxylamine. Inhibited chymotrypsin regained 40-85% of activity and inhibited rat granule chymase regained 30-100% of activity in the presence of hydroxylamine.

Table VII shows the inhibition of PPE, HLE, chymotrypsin and cathepsin G by isocoumarins substituted with bromoalkoxy groups. The structure with R group of R-methylbenzylcarbamylamino, Y group of Cl and Z group of bromoethoxy is the best inhibitor for PPE. It is unexpected that all the compounds with Y group of Cl, Z-group of bromoethoxy are potent inhibitors of HLE, especially the structure with R group of phenylcarbamoylamino is the most potent inhibitor of HLE. The structures with R group of $NO_2$, Y group of Cl, Z group of 2-bromoisopropoxy and R group of phenylacetyl, Y group of Cl, Z-group of bromopropoxy are the best at inhibiting chymotrypsin.

Table VIII shows the half-life for the deacylation of inactivated elastase by substituted isocoumarins. Only the enzyme inactivated by compound with R group of phenylcarbamyl, Y group of Cl, and Z group of methoxy is stable with the half-life more than 48 hrs.

Pulmonary emphysema is a disease characterized by progressive loss of lung elasticity due to the destruction of lung elastin and alveoli. The destructive changes of lung parentchyma associated with pulmonary emphysema are caused by uncontrolled proteolysis in lung tissues (Janoff, Chest 83 pp 54-58 (1983)). A number of proteases has been shown to induce emphysema in animals (Marco et al., Am. Rev. Respir. Dis. 104, pp 595-598 (1971); Kaplan, J. Lab. Clin. Med. 82, pp 349-356 (1973)), particularly human leukocyte elastase (Janoff, ibid 115, pp 461-478 (1977)). Leukocyte elastase and other mediators of inflammation also appear to play a role in diseases such as mucocutaneous lymph node syndrome (Reiger et al., Eur. J. Pediatr. 140, pp 92-97 (1983) and adult respiratory distress syndrome (Stockley, Clinical Science 64, pp 119-126 (1983); Lee et al., N. Eng. J. Med. 304, pp 192-196 (1981); Rinaldo, ibid 301, 900-909 (1982)).

It is known that in vitro activity of elastase inhibitors correlates with in vivo activity in animal models of emphysema and inflammation (Otterness et al., editor, Advances in Inflammation Research, Vol. 11, Raven Press 1986, and this article is incorporated herein by reference). Prophylactic administration of an inhibitor of elastase significantly diminishes the extent of elastase-induced emphysema (Kleinerman et al., Am. Rev. Resir. Dis. 121, pp 381-387 (1980); Lucey et al., Eur. Respir. J. 2, pp 421-427 (1989)). Thus the novel inhibitors described here should be useful for the treatment of emphysema and inflammation. Elastase inhibitors have been used orally, by injection or by instillation in the lungs in animal studies (Powers, Am. Rev. Respir. Dis., 127, s54-s58 (1983); Powers and Bengali, Am. Rev. Respir. Dis. 134, pp 1097-1100 (1986) and these two articles are incorporated herein by reference). The inhibitors described above can be used by any of these routes.

For treatment of inflammation, the compounds of Formula (I) may be administered orally, topically or parenterally. The term parenteral as used includes subcutaneous injection, intravenous, intramuscular, intrasternal injection or infusion techniques. The dosage depends primarily on the specific formulation and on the object of the therapy or prophylaxis. The amount of the individual doses as well as the administration is best determined by individually assessing the particular case.

The pharmaceutical compositions containing the active ingredient may be in a form suitable for oral use, for example as tablets, troches, lozenges, aqueous or oily suspensions, dispersible powders or granules, emulsions, hard or soft capsules or syrups or elixirs. Dosage levels of the order to 0.2 mg to 140 mg per kilogram of body weight per day are useful in the treatment of above-indicated conditions (10 mg to 7 gms per patient per day). The amount of active ingredient that may be combined with carrier materials to produce a single dosage form will vary depending upon the host treated and the particular mode of administration.

For injection, the therapeutic amount of the compounds of Formula (I) or their pharmaceutically acceptable salts will normally be in the dosage range from 0.2 to 140 mg/kg of body weight. Administration is made by intravenous, intramuscular or subscutaneous injection. Accordingly, pharmaceutical compositions for parenteral administration will contain in a single dosage form about 10 mg to 7 gms of compounds of Formula (I) per dose. In addition to the active ingredient, these pharmaceutical compositions will usually contain a buffer, e.g. a phosphate buffer which keeps the pH in the range from 3.5 to 7 and also sodium chloride, mannitol or sorbitol for adjusting the isotonic pressure.

A composition for topical application can be formulated as an aqueous solution, lotion, jelly or an oily solution or suspension. A composition in the form of an aqueous solution is obtained by dissolving the compounds of Formula (I) in aqueous buffer solution of pH 4 to 6.5 and if desired, adding a polymeric binder. An oily formulation for topical application is obtained by suspending the compounds of Formula (I) in an oil, optionally with the addition of a swelling agent such as aluminium stearate and/or a surfactant.

To use the above inhibitors in vitro, they are dissolved in an organic solvent such as dimethylsulfoxide or ethanol, and are added to an aqueous solution containing serine proteases. The final concentration of the organic solvent should be less than 25%. The inhibitors may also be added as solids or in suspension. The serine protease inhibitors of this invention would be useful in a variety of experimental procedures where proteolysis is a significant problem. Inclusion of these inhibitors in a radioimmunoassay experiments would result in higher sensitivity. The use of these inhibitors in plasma fractionation procedures would result in higher yields of valuable plasma proteins and would make purification of the proteins easier. The inhibitors disclosed here could be used in cloning experiments utilizing bacterial cultures, yeast and purified cloned product in higher yield.

The following examples are given to illustrate the invention and are not intended to limit it in any manner.

EXAMPLE 1

Preparation of 7-heptafluorobutyroylamino-4-chloro-3-methoxyisocoumarin

7-Amino-4-chloro-3-methoxyisocoumarin (1 eq.) and heptafluorobutyryl chloride (1.5 eq.) were dissolved in THF and then $Et_3N$ (1.5 eq.) was added dropwise to the stirred mixture over a period of 4 h. After addition of $Et_3N$ was completed, the reaction mixture was stirred for 20 h at r.t., then the solvent was removed in vacuo and the residue dissolved in ethyl acetate. This solution was washed with water, 10% citric acid, 4% $NaHCO_3$ and finally again with water, dried over $MgSO_4$ and evaporated. The residue was crystallized from THF-hexane to give yellow solid; yield 62%; mp 189°-190° C.; MS, m/e 421 (M+). Anal. Calc. for $C_{14}H_7F_7ClNO_4$: C, 39.84; H, 1.66; N, 3.32. Found: C, 40.24; H, 1.70; N, 3.33.

7-(3-fluorobenzoyl)amino-4-chloro-3-propoxyisocoumarin, 7-(4-methoxybenzoyl)amino-4-chloro-3-propoxyisocoumarin, 7-heptafluorobutyroylamino-4-chloro-3-ethoxyisocoumarin, 7-heptafluorobutyroylamino-4-chloro-3-(2-bromoethoxy)isocoumarin, 7-heptafluorobutyroylamino-4-chloro-3-(2-phenylethoxy)isocoumarin, 7-(3-fluorobenzoyl)amino-4-chloro-3-(2-bromoethoxy)isocoumarin, 7-(3-nitrobenzoyl)amino-4-chloro-3-(2-bromoethoxy)isocoumarin, 7-(α-toluenesulfonyl)amino-4-chloro-3-(2-bromoethoxy)isocoumarin can be prepared by the same procedure.

EXAMPLE 2

Preparation of 7-[(3-phenylglutaryl)amino]-4-chloro-3-methoxyisocoumarin

One gram of 7-amino-4-chloro-3-methoxyisocoumarin dissolved in 15 ml of pyridine was treated with 4 equivalents of 3-phenylglutaric anhydride. After 5 hrs, 3 ml of water were added to the reaction mixture. Partial evaporation of the solvents left a semisolid residue, which was diluted with a mixture of acetone and water (3:1), and filtered. The crude crystals were then recrystallized from acetone/water to give yellow crystals, yield 62%.; mp 105°-106° C.; MS (FAB+) m/e 416 (M+ +1). Anal. Calc. for $C_{21}H_{18}ClNO_6 \cdot 1.2H_2O$: C, 57.66; H, 4.42; Cl, 3.20. Found: C, 57.60; H, 4.77; N, 3.17.

7-(o-phthalyl)amino-4-chloro-3-ethoxyisocoumarin and 7-(o-phthalyl)amino-4-chloro-3-(2-phenylethoxy)isocoumarin can be prepared by the same procedure.

EXAMPLE 3

Preparation of 7-[(methoxyglutaryl)amino]-4-chloro-3-methoxyisocoumarin

7-Glutarylamino-4-chloro-3-methoxyisocoumarin was prepared by the same procedure described in example 2, mp 194° C. (dec.); MS m/e 339 (M+). Anal. Calc. for $C_{15}H_{14}ClNO_6 \cdot 1.2 H_2O$: C, 57.66; H, 4.42; N, 3.20. Found: C, 57.60; H, 4.77; N, 3.17. An ethereal solution containing 2.5 mmoles of diazomethane was added to a solution of 0.6 mmoles of 7-glutarylamino-4-chloro-3-methoxyisocoumarin in a mixture of DMF and ethyl acetate. After 30 min, the reaction mixture was evaporated to dryness and the crude ester crystallized from acetone, giving a yellow solid, mp 147°-151° C. (dec.); MS m/e 353 (M+). Anal. Calc. for $C_{16}H_{16}ClNO_6$: C, 54.30; H, 4.56; N, 3.96; Cl, 10.03. Found: C, 54.39; H, 4.58; N, 3.39; Cl, 10.13.

7-(methoxysuccinyl)amino-4-chloro-3-ethoxyisocoumarin and 7-(methoxysuccinyl)amino-4-chloro-3-(2-phenylethoxy)isocoumarin was prepared by the same procedure.

EXAMPLE 4

Preparation of 7-[(N-tosyl-α-phenylglycyl)amino]-4-chloro-3-methoxyisocoumarin N-Tosyl phenylglycine (1.8 mmole) was dissolved in 2 ml of $SOCl_2$ and stirred at reflux temperature for 40 min. The reaction mixture was concentrated to dryness in vacuo and the residue triturated with EtOAc/Hexane (3:1) to yield the acid chloride (94%) which is used in the next step without further purification. Tosphenylglycine acid chloride (155 mg) and 7-amino-4-chloro-3-methoxyisocoumarin (72 mg) were dissolved in a mixture of methylene chloride (1 ml) and THF (1 ml). A solution of triethylamine (0.06 ml in 2 ml of $CH_2Cl_2$) was added dropwise and the reaction mixture was stirred at room temperature for 2 h. The solvent was removed in vacuo and the residue was triturated with ethyl acetate (1.5 ml). The resulting yellow solid was recrystallized from THF/$H_2O$ to yield 108 mg (66%); mp 150°-151° C. (dec.); MS, m/e 512 (M+). Anal. Calc. for $C_{25}H_{21}ClN_2O_6S$: C, 58.53; H, 4.13; N, 5.46. Found: C, 58.43; H, 4.15; N, 5.40.

EXAMPLE 5

Preparation of 7-(N-phenylcarbamoylamino)-4-chloro-3-methoxyisocoumarin

This compound was prepared by reaction of 110 mg (0.5 mmol) of 7-amino-4-chloro-3-methoxyisocoumarin with 60 mg (0.5 mmol) of phenyl isocyanate at room temperature in $CH_2Cl_2$ for 24 h. After standard work-up, this isocoumarin was obtained as yellow crystals; mp 203°-204° C.; MS, m/e 344 (M+). Anal. Calc. for $C_{17}H_{13}ClN_2O_4$: C, 59.23; H, 3.08; N, 8.13; Cl, 10.28. Found: C, 59.28; H, 3.82; N, 8.11; Cl, 10.35.

7-benzylamino-4-chloro-3-ethoxyisocoumarin and 7-benzylamino-4-chloro-3-(2-phenylethoxy)isocoumarin can be prepared by the same procedure.

EXAMPLE 6

Preparation of 4-chloro-7-phenylthiocarbamoylamino-3-ethoxyisocoumarin

This compound was preparation by reaction of 7-amino-4-chloro-3-ethoxyisocoumarin with phenyl isothiocyanate at r.t. in THF for 24 hrs. The product was obtained as yellow solid: yield 55%, m.p. 176°-177° C. (dec.); TLC, $R_f$=0.76 ($CH_3Cl$:MeOH=9:1), MS m/e=374 (M+). Anal. Calcd. for $C_{18}H_{15}N_2O_3ClS$: C, 57.62; H, 4.00. Found: C, 57.77; H, 4.04.

EXAMPLE 7

Preparation of 7-dihydrocinnamoylamino-4-chloro-3-propyloxyisocoumarin

This compound was synthesized by reaction of equimolar of 7-amino-4-chloro-3-propoxyisocoumarin, dihydrocinnamic acid chloride and triethylamine in dry THF. The reaction mixture was stirred overnight, and the solution was washed with water, 4% NaHCO$_3$, water and dried over MgSO$_4$. After filtration and evaporation, a yellow residue was crystallized from THF-pentane, yield 81%; mp 182°-184° C.; TLC, R$_f$=0.74 (CH$_3$Cl:MeOH=9:1); MS, m/e 385 (M+). Anal. Calc for C$_{21}$H$_{20}$O$_4$NCl.0.5H$_2$O: C, 63.81; H, 5.32. Found: C, 63.47; H, 5.30.

7-phenoxycarbonylamino-4-chloro-3-ethoxyisocoumarin and 7-phenoxycarbonylamino-4-chloro-3-(2-phenylethoxy)isocoumarin can be prepared by the same procedure.

EXAMPLE 8

Preparation of 7-(Boc-valyl)amino-4-chloro-3-propyloxyisocoumarin

This compound was synthesized by reaction of an equimolar amount of 7-amino-4-chloro-3-propoxyisocoumarin and Boc-Val anhydride in THF. The reaction mixture was stirred overnight. The work-up as described above gives a yellow solid which was recrystallized from THF-pentane, yield 48%: mp 171°-173° C.; TLC, R$_f$=0.8 (CH$_3$Cl:MeOH=9:1); MS, m/e 452 (M+). Anal. Calc. for C$_{22}$H$_{29}$O$_6$N$_2$Cl: C, 58.35; H, 6.41; N, 6.19; Cl, 7.83. Found: C, 58.40; H, 6.47; N, 6.20; Cl, 7.79.

7-(Boc-phenylalanyl)amino-4-chloro-3-propyloxyisocoumarin, 7-(benzoylalanylalanyl)amino-4-chloro-3-propyloxyisocoumarin, 7-(Boc-valyl)amino-4-chloro-3-ethoxyisocoumarin, 7-(Boc-alanyl)amino-4-chloro-3-ethoxyisocoumarin and 7-(Boc-alanyl)amino-4-chloro-3-(2-phenylethoxy)isocoumarin can be prepared by the same procedure.

EXAMPLE 9

Preparation of 7-ethylcarbamoylamino-4-chloro-3-propyloxyisocoumarin

This compound was synthesized by the reaction of an equimolar amount of 7-amino-4-chloro-3-propoxyisocoumarin and ethyl isocyanate in small amount of dry THF. The reaction mixture was stirred at r.t. for a few days. During this time the yellow crystals slowly crystallized out. After filtration, the compounds were recrystallized once more from THF-pentane, yield 45%; mp 189°-191° C.; TLC, R$_f$=0.43 (CH$_3$Cl:MeOH=9:1); MS, m/e 324 (M+). Anal. Calc. for C$_{15}$H$_{17}$O$_4$N$_2$Cl: C, 55.42; H, 5.23. Found: C, 55.31; H, 5.28.

EXAMPLE 10

Preparation of 7-amino-4-chloro-3-(2-bromoethoxy)isocoumarin

This compound was prepared by cyclization of 1 equivalent of bromoethyl nitrohomophthalate with 2.5 equivalent of PCl$_5$, followed by catalytic reduction of the nitro group. The product was yellow solid, mp 134°-137° C.; MS, m/e 317 (M+). Anal. Calc. for C$_{11}$H$_9$NO$_3$ClBr: C, 41.44; H, 2.83, N, 4.40. Found: C, 42.11; H, 2.87; N, 4.46.

EXAMPLE 11

Preparation of 7-(phenylcarbamoylamino)-4-chloro-3-(2-bromoethoxy)isocoumarin

7-Amino-3-(2-bromoethoxy)-4-chloroisocoumarin was synthesized as described above. This compound (0.32 g, 1 mmole) was mixed with phenylisocyanate (0.12 g, 1 mmole) in 5 ml of THF and the reaction mixture was stirred at r.t. overnight. The product 7-(phenylcarbamoylamino)-4-chloro-3-(2-bromoethoxy)isocoumarin precipitated out, yield 40%, mp. 215°-217° C.; MS, m/e 437.9 (M+). Anal. Calc. for C$_{18}$H$_{14}$N$_2$O$_4$ClBr: C, 49.40; H, 3.22; N, 6.40; Cl, 8.10. Found: C, 49.48; H, 3.25; N, 6.34; Cl, 8.12.

7-(4-Fluorobenzyl)thiocarbamoylamino-4-chloro-3-(2-bromoethoxy)isocoumarin, and 7-(2,4-dimethylbenzyl)thiocarbamoylamino-4-chloro-3-(2-bromoethoxy)isocoumarin and 7-(4-fluorobenzyl)thiocarbamoylamino-4-chloro-3-(2-phenylethoxy)isocoumarin can be prepared by the same procedure.

EXAMPLE 12

Preparation of 7-(acetylamino)-4-chloro-3-(3-bromopropoxy)isocoumarin

7-Amino-3-(3-bromopropoxy)-4-chloroisocoumarin was synthesized similarly as described in Example 10. This compound (0.33 g, 1 mmole) was heated with 0.15 g of acetic anhydride (1.5 mmole) in 20 ml of dry THF. After a few minutes, yellow solid was precipitated out. After 3 hrs, the solution was concentrated to 5 ml, and the solid was filtered to give 0.37 g of 7-(acetylamino)-4-chloro-3-(3-bromopropoxy)isocoumarin, mp. 170°-172° C.; MS, m/e 375 (M+). Anal. Calc. for C$_{14}$H$_{13}$NO$_4$ClBr: C, 44.89; H, 3.50. Found: C, 44.95; H, 3.54.

EXAMPLE 13

Preparation of 7-(R-α-methylbenzylcarbamoylamino)-4-chloro-3-(2-bromoethoxy)isocoumarin This compound was synthesized by the reaction of 7-amino-4-chloro-3-(2-bromoethoxy)isocoumarin with R-α-methylbenzyl isocyanate as described above, mp. 183°-185° C.; MS m/e 464 (M+). Anal. Calc. for C$_{20}$H$_{18}$N$_2$O$_4$ClBr: C, 51.58; H, 3.90. Found: C,51.66; H, 3.90.

EXAMPLE 14

Preparation of 7-(Boc-D-phenylalanylamino)-4-chloro-3-(2-bromoethoxy)isocoumarin Boc-D-Phe (0.33 g, 1.2 mmole) reacted with 1,3-dicyclohexylcarbodiimide (0.13 g, 0.6 mmole) in 10 ml THF at 0° C. for 1 hr to form the symmetric anhydride, and then 7-amino-4-chloro-3-(2-bromoethoxy)isocoumarin (0.2 g, 0.6 mmole) was added. The reaction was stirred at r.t. overnight and 7-(Boc-D-phenylamino)-4-chloro-3-(2-bromoethoxy)isocoumarin was precipitated out (0.29 g, 71%), mp. 180°-182° C.; TLC, R$_f$=0.95 (CH$_3$Cl:MeOH=9:1); MS m/e=566 (M+). Anal. Calc. for C$_{25}$H$_{26}$N$_2$O$_6$ClBr: C, 53.07; H, 4.63; N, 4.95; Cl 6.27. Found: C,53.25; H, 4.66; N, 4.87; Cl, 6.24.

7-(Benzoyl-L-alanylamino)-4-chloro-3-(2-bromoethoxy)isocoumarin and 7-(benzoyl-L-alanylamino)-4-chloro-3-(2-phenylethoxy)isocoumarin can be prepared by the same procedure.

7-(D-Phenylalanylamino)-4-chloro-3-(2-bromoethoxy)isocoumarin and 7-(alanylalanylamino)-4-chloro-3-(2-bromoethoxy)isocoumarin can be prepared by deblocking the Boc group of 7-(Boc-D-phenylalanylamino)-4-chloro-3-(2-bromoethoxy)isocoumarin and 7-(Boc-D- alanylalanylamino)-4-chloro-3-(2-bromoethoxy)isocoumarin with trifluoroacetic acid.

EXAMPLE 15

Preparation of 7-dansylamino-4-chloro-3-(2-bromoethoxy)isocoumarin

Dansyl chloride (0.17 g, 0.63 mmole) was mixed with 7-amino-4-chloro-3-(2-bromoethoxy)isocoumarin (0.2 g, 0.63 mmole) in 5 ml of THF, and Et$_3$N (0.065 g) was then added. The reaction mixture was stirred at r.t. for a few days, and a yellow solid precipitated out. The final product was crystallized from THF/hexane, yield 41%, mp 114°–117° C.; MS, m/e 552 (M$^+$+1). Anal. Calc. for C$_{23}$H$_{21}$N$_2$O$_5$ClBrS.1.5H$_2$O: C, 47.63; H, 4.14. Found: C, 47.41; H, 4.27.

7-(p-Toluenesulfonyl)amino-4-chloro-3-(2-bromoethoxy)isocoumarin and 7-(p-toluenesulfonyl)amino-4-chloro-3-(2-phenylethoxy)isocoumarin can be prepared by the same procedure.

EXAMPLE 16

Preparation of 7-(biotinylamino)-4-chloro-3-(2-phenylethoxy)isocoumarin

Biotin acid chloride was prepared by incubating 0.4 g of biotin in 6 ml of thionyl chloride at 25°–35° C. for 1 hr, and excess thionyl chloride was removed under vacuum. The acid chloride was used for the next step without further purification. Biotin acid chloride and 7-amino-4-chloro-3-(2-phenylethoxy)isocoumarin (0.26 g) was dissolved in small amount of DMF, and then Et$_3$N (0.08 g) were added. The reaction mixture was stirred at r.t. overnight. The product was purified by column chromatography, yield 0.1 g, mp 182°–185° C.; TLC, R$_f$=0.25 (CH$_2$Cl$_2$:MeOH=15:1). Anal. Calc. for C$_{27}$H$_{28}$N$_3$O$_5$ClS.0.25 H$_2$O: C, 59.39; H, 5.22, N, 7.70. Found: C, 59.08; H, 5.37; N, 7.94.

7-(Biotinylamino)-4-chloro-3-(pentafluoropropoxy)isocoumarin can be prepared by the same procedure.

EXAMPLE 17

Preparation of 7-[(6-biotinylamino)caproyl]amino-4-chloro-3-(2-phenylethoxy)isocoumarin 6-(Biotinylamino)caproic acid was prepared from N-hydroxysuccinimido biotinate (Jasiewicz et al., Exp. Cell Res. 100, pp 213–217 (1976)) and methyl 6-aminocaproic acid hydrochloride by a previously described method (Hofmann et al., Biochemistry 23, pp 2547–2553 (1984)). 6-(Biotinylamino)caproic acid chloride was synthesized and reacted with 7-amino-4-chloro-3-(2-phenylethoxy)isocoumarin as described above. The product was purified by column chromatography, mp 163°–167° C. Anal. Calc. for C$_{33}$H$_{39}$N$_4$O$_6$ClS.H$_2$O: C, 58.72; H, 6.22; N, 8.96; Cl, 5.59. Found: C, 58.87; H, 6.14; N, 8.32; Cl, 5.27.

TABLE I

Inhibition Constants for Inactivation of Elastases by 7-substituted-4-chloro-3-methoxyisocoumarins$^a$.

| Compounds 7-Substituent | HLE | | PPE | |
| --- | --- | --- | --- | --- |
| | [I] ($\mu$M) | k$_{obs}$/[I] (M$^{-1}$s$^{-1}$) | [I] ($\mu$M) | k$_{obs}$/[I] (M$^{-1}$s$^{-1}$) |
| NCO | 1.8 | 9,200 | 8.3 | 650 |
| EtOCONH | 2.3 | 47,000 | 8.3 | 2,000 |
| PhOCONH | 1.8 | 13,000 | 8.8 | 850 |
| PhCH$_2$OCONH | 1.6 | 71,000 | 136.0 | 260 |
| H$_2$NCONH | | | 8.2 | 2,100 |
| CH$_3$NHCONH | 3.3 | 9,460 | 13 | 1,300 |
| EtNHCONH | | | 6.3 | 1,700 |
| i-PrNHCONH | 3.0 | 9,000 | 12 | 2,300 |
| t-BuNHCONH | 6.6 | 20,000 | 13 | 3,200 |
| PhNHCONH | 2.0 | 49,000 | 8.3 | 7,300 |
| PhCH$_2$(PhCH$_2$CH$_2$)NCONH | 2.2 | 12,000 | 490.0 | 17 |
| C$_3$F$_7$CONH | 2.7 | 47,000 | 17.0 | 1,100 |
| Fmoc-NH | 2.5 | 10,000 | 600.0 | 20 |
| Tos-Phenylglycyl-NH | 1.6 | 84,000 | 8.3 | 1,500 |
| o-HOOCC$_6$H$_4$CONH | 1.8 | 52,000 | 17.0 | 2,700 |
| o-CH$_3$OOCC$_6$H$_4$CONH | — | — | 8.3 | 7,100 |
| CH$_3$OOCCH$_2$CH$_2$CONH | 2.3 | 43,000 | 17.0 | 2,200 |
| CH$_3$OOCCH$_2$CH$_2$CH$_2$CONH | 2.3 | 54,000 | 8.3 | 2,800 |
| HOOCCH$_2$CH(Ph)CH$_2$CONH | 1.6 | 66,000 | 8.3 | 3,100 |
| m-CH$_3$OOCNHC$_6$H$_4$CONH | 1.4 | 100,000 | 17.0 | 2,500 |

$^a$Inhibition constants were in 0.1 M Hepes, 0.5 M NaCl, pH 7.5 buffer, 8–9% Me$_2$SO and at 25° C.

TABLE II

Inhibition Rates of Inactivation of Porcine Pancreatic Elastase by 7-Substituted-4-chloro-3-ethoxyisocoumarin$^a$.

| Compounds 7-Substituent | [I] ($\mu$M) | k$_{obs}$/[I] (M$^{-1}$s$^{-1}$) |
| --- | --- | --- |
| EtO-CO-NH | 9.6 | 3,500 |
| Et-NH-CS-NH | 20–50 | 4,200 |
| Ph-NH-CS-NH | 9–31 | 12,000 |

$^a$Inhibition rates were measured in 0.1 M Hepes, 0.5 M NaCl, 8.3% Me$_2$SO, pH 7.5 and at 25° C.

TABLE III

Inhibition Rates of Inactivation of Serine Proteases by Derivatives of 7-Subsitituted-4-chloro-3-propyloxyisocoumarins$^a$.

| Compounds 7-Substituted | k$_{obs}$/[I] (M$^{-1}$s$^{-1}$) | | | |
| --- | --- | --- | --- | --- |
| | PPE$^b$ | HLE$^c$ | Chymotrypsin$^d$ | Cathepsin G$^e$ |
| PhCH$_2$CH$_2$CONH | | >250,000 | | 20 |
| CH$_3$CH$_2$OCONH | 220 | >181,000 | 12,000 | 138 |
| CH$_3$CH$_2$NHCONH | 1,600 | >276,000 | 5,200 | 166 |

TABLE III-continued

Inhibition Rates of Inactivation of Serine Proteases by Derivatives of 7-Susbitituted-4-chloro-3-propyloxyisocoumarins[a].

| Compounds 7-Substituted | $k_{obs}/[I]$ (M$^{-1}$s$^{-1}$) | | | |
|---|---|---|---|---|
| | PPE[b] | HLE[c] | Chymotrypsin[d] | Cathepsin G[e] |
| PhNHCONH | 80 | 143,000 | 120 | NI |
| PHNHCSNH | 520 | >166,000 | 6,100 | |
| PhCH$_2$NHCSNH | | >131,000 | | |
| 3-NO$_2$—C$_6$H$_4$CONH | | >210,000 | | 4 |
| CH$_3$SCH$_2$CONH | | >152,000 | | 28 |
| Boc-Val-NH | | 64,000 | | 17 |

[a]Inhibition rates were measured in 0.1 M Hepes, 0.5 M NaCl, 2.5% Me$_2$SO, pH 7.5 and at 25° C.
[b]Inhibitor concentrations were 34–56 μM.
[c]Inhibitor concentrations were 0.7–1.9 μM.
[d]Inhibitor concentrations were 3.4–70 μM.
[e]Inhibitor concentrations were 8.7–87 μM.

TABLE IV

Inhibition of Serine Proteases by Biotin-Isocoumarin Derivatives[a].

| Compounds | $k_{obs}/[I]$ (M$^{-1}$s$^{-1}$) | | | |
|---|---|---|---|---|
| | Chymotrypsin[b] | Cat. G[c] | HLE[d] | PPE[e] |
| 7-biotinylamino-4-chloro-3-(2-phenylethoxy)isocoumarin | 330 165 | NI | 740 | NI |
| 7-biotinylamino-4-chloro-3-propoxyisocoumarin | 65 | 6.7 | 19,900 | 470 |
| 7-(6-biotinylaminocaproyl)amino-4-chloro-3-(2-phenylethoxy)isocoumarin | 1,080 190 | 13% | 670 | NI[f] |
| 7-(6-biotinylaminocaproyl)amino-4-chloro-3-propoxyisocoumarin | 260 | 3.3 | 76,700 | 350 |
| 7-(6-biotinylaminocaproyl)amino-4-chloro-3-ethoxyisocoumarin | 260 | 59 | 96,000 | 520 |

[a]Inhibition was measured in 0.1 M Hepes, 0.5 M NaCl, pH 7.5 buffer, 5–10% Me$_2$SO and at 25° C. Suc-Val-Phe-NA (0.48 mM) was used as the substrate for chymotrypsin and cat G. MeO-Suc-Ala-Ala-Pro-Val-NA (0.24–0.47 mM) and Suc-Ala-Ala-Ala-NA (0.29–0.48 mM) were used as the substrate for HLE and PPE respectively.
[b]Inhibitor concentrations were 20–400 μM.
[c]Inhibitor concentrations were 75–400 μM.
[d]Inhibitor concentrations were 2.0–78 μM.
[e]Inhibitor concentrations were 38–78 μM.
[f]No inhibition.

TABLE V

Inhibition of Rat granule Serine Proteases by Biotin-Isocoumarin Derivatives[a].

| Compounds | [I] (mM) | Rat Granule Chymase % of inhibition[b] | Rat Granule Tryptase $k_{obs}/[I]$ (M$^{-1}$s$^{-1}$) |
|---|---|---|---|
| 7-(6-Biotinylaminocaproyl)amino-4-chloro-3-(2-phenylethoxy)isocoumarin | 0.078 | 30–50 | 6–12 |
| 7-Biotinylamino-4-chloro-3-(2-phenylethoxy)isocoumarin | 0.2 | 10–20 | 2–3 |

[a]Inhibition was measured at 0.1 M Hepes, 0.5 M NaCl, pH 7.5 buffer, 10% Me$_2$SO and 25° C. Suc-Phe-Leu-Phe-SBzl (0.14 mM) and Z-Gly-Arg-SBzl (0.06 mM) were used to measure chymase and tryptase activity respectively.
[b]Inhibition was not time dependent.

TABLE VI

Reactiviation of Inhibited Chymotrypsin and Rat Granule Chymase by Biotin-Isocoumarin Derivatives in Buffer and in the Presence of NH$_2$OH[a].

| Inhibitor | [I] (μM) | % of Enzyme Activity Reactivated | | |
|---|---|---|---|---|
| | | Chymotrypsin | | Rat granule chymase |
| | | in buffer[b] | +NH$_2$OH | +NH$_2$OH |
| 7-(6-Biotinylaminocaproyl)amino-4-chloro-3-(2-phenylethoxy)isocoumarin | 39 | 6 | 50 | |
| | 78 | 0 | 40 | 30–50 |
| 7-Biotinylamino-4-chloro-3-(2-phenylethoxy)isocoumarin | 39 | 51 | 85 | |
| | 78 | 7 | 79 | 100 |

[a]Inhibition was performed at 0.1 M Hepes, 0.5 M NaCl, pH 7.5 buffer, 10% Me$_2$SO and 25° C. Reactivation was carried out in the presence of 0.36 M of NH$_2$OH, and occurred immediately after the addition of NH$_2$OH.
[b]Enzyme activity was measured after two days.

TABLE VII

Inhibition Rates of Serine Proteases by 7-substituted-4-chloro-3-bromoalkoxyisocoumarins and 7-amino-4-chloro-3-alkoxyisocoumarins[a].

| Compounds | $k_{obs}/[I]$ (M$^{-1}$s$^{-1}$) | | | |
|---|---|---|---|---|
| | PPE[b] | HLE[c] | Chymotrypsin[d] | Cathepsin G[e] |
| (I) 7-substituted-4-chloro-3-(2-bromoethoxy)isocoumarin | | | | |

TABLE VII-continued

Inhibition Rates of Serine Proteases by 7-substituted-4-chloro-3-bromoalkoxyisocoumarins and 7-amino-4-chloro-3-alkoxyisocoumarins[a].

| Compounds | $k_{obs}/[I]$ $(M^{-1}s^{-1})$ | | | |
|---|---|---|---|---|
| | PPE[b] | HLE[c] | Chymotrypsin[d] | Cathepsin G[e] |
| 7-NH$_2$ | 1,000 | 200,000[f] | 1,160 | 410 |
| 7-NO$_2$ | 6,330 | 65,600 | 98,000[g] | 710 |
| 7-(t-Bu-NH-CO-NH) | 6,600 | | 320 | 56 |
| 7-(isopropyl-NH-CO-NH) | 4,470 | 646,000[g] | 1340[H] | 77 |
| 7-(Ph-NH-CO-NH) | 36 | 1,200,000[g] | 12 | NI[i] |
| 7-(Ph-CH$_2$-NH-CO-NH) | 3,010 | 480,000[g] | 890 | 23%[j] |
| 7-(R-(C$_6$H$_5$)(CH$_3$)CH-NH-CO-NH) | 9,900 | >440,000[g] | 180[h] | 77 |
| 7-(S-(C$_6$H$_5$)(CH$_3$)CH-NH-CO-NH) | 2,660 | >570,000[g] | 440 | 21%[j] |
| 7-(Naphthyl-NH-CO-NH) | 76 | 390,000[g] | 80 | 22%[j] |
| 7-((CH$_3$)$_3$C-CH$_2$CO-NH) | 3,650 | | 1,070 | 240 |
| 7-(Ph-CH$_2$-CO-NH) | 4,950 | 480,000[g] | 82,000[g] | 70 |
| 7-(Boc-D-Phe-NH) | 30 | | 150 | 19%[j] |
| 7-(Boc-L-Phe-NH) | 50 | | 400 | 19%[j] |
| 7-(Boc-Ala-Ala-NH) | 1,670 | 230,000[g] | 2,750[h] 810[h] | 46 |
| 7-(PhNHCSNH) | 1,250 | >480,000[g] | 39,000[g] | 200 |
| 7-(m-COOH-PhNHCSNH) | | >240,000[g] | 1,960 | 320 |
| 7-(p-COOH-PhNHCSNH) | | >390,000[g] | 1,720 | 450 |
| (II). 7-substituted-4-chloro-3-(3-bromopropoxy)isocoumarin | | | | |
| 7-NH$_2$ | 10 | 4,000 | 790 | 210 |
| 7-NO$_2$ | | | | |
| 7-(Ph-NH-CO-NH) | 4 | 13,750[h] 2,890[h] | 180 | 17%[j] |
| 7-(Ph-CH$_2$-NH-CO-NH) | 13 | 15,650 | 440 | 21%[j] |
| 7-(CH$_3$-CO-NH) | 24 | 24,400 | 3,980 | 170 |
| 7-(Ph-CH$_2$-CO-NH) | 28 | 32,350 | 140,000[g] | 28%[j] |
| 7-(Ph-CH$_2$CH$_2$CO-NH) | | 35,650[h] 9,870[h] | 600 | NI |
| 7-(Boc-D-Phe-NH) | | 1,480 | 70 | NI |
| 7-(Boc-L-Phe-NH) | | 1,320 | 490 | NI |
| (III). 7-substituted-4-chloro-3-(2-bromoisopropoxy)isocoumarin | | | | |
| 7-NO$_2$ | 1,060 | | 200,000[g] | 1,660 |
| 7-NH$_2$ | 62 | 24,000 | 320 | 150 |
| (IV). 7-amino-4-chloro-3-alkoxyisocoumarin | | | | |
| 3-CH$_3$CH$_2$CH$_2$O | 4.3 | 390 | 375 | 61 |
| 3-CH$_3$CH$_2$CH$_2$OCH$_2$CH$_2$O | 0.5 | 33 | 140 | 2.6 |

[a]Inhibition rates were measured in 0.1 M Hepes, 0.5 M NaCl, pH 7.5 buffer, 8–9% Me$_2$SO and at 25° C. Substrates were Suc-Ala-Ala-Ala-NA (0.48 mM) for PPE; MeO-Suc-Ala-Ala-Pro-Val-NA (0.24 mM) for HLE; Suc-Val-Pro-Phe-NA (0.48 mM) for chymotrypsin and cathepsin G.
[b]Inhibitor concentrations were 0.04–2.0 mM.
[c]Inhibitor concentrations were 0.07–710 mM.
[d]Inhibitor concentrations were 1.7–58 mM.
[e]Inhibitor concentrations were 35–710 mM.
[f]Progress curve method was used according to Tian & Tsou (1982) Biochemistry 21, 1028–1032.
[g]Second order rate constant was obtained using equimolar concentration of inhibitor and enzyme.
[h]Biphasic plot was obtained, and two inhibition rates were shown.
[i]NI = No inhibition.
[j]Percentage of inhibition was obtained after 5 min incubation of inhibitor with enzyme.

TABLE VIII

Half-Lives for Deacylation of Elastases Inactivated by 7-Substituted-4-chloro-3-methoxyisocoumarins[a].

| Compounds | $t_{\frac{1}{2}}$ (h) | |
|---|---|---|
| 7-Substituted | HLE | PPE |
| HOOCCH$_2$CH$_2$CONH | 1.5 | 1.3 |
| HOOCCH$_2$CH$_2$CH$_2$CONH | 1.7 | 1.5 |
| o-HOOCC$_6$H$_4$CONH | 5.0 | 17 |
| CH$_3$OOCCH$_2$CH$_2$CH$_2$CONH | 1.0 | 1.0 |
| PhNHCONH | >48 | >48 |

[a]Enzyme activity was followed after removal of excess inhibitors by centrifugation using Amicon centricon-10 microconcentrator.

What is claimed is:

1. A compound of the formula:

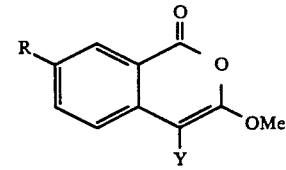

or a pharmaceutically acceptable salt thereof, wherein R is selected from the group consisting of O=C=N—, S=C=N—, M—NH—, M—O—,
wherein M represents NH$_2$—CO—, NH$_2$—CS—, NH$_2$—SO$_2$—, X—NH—CO—, X—NH—CS—, X—NH—SO$_2$—, X—CS—, X—SO$_2$—, X—O—CO—, X—O—CS—, or D—CO—,
wherein X represents C$_{1-6}$ alkyl, C$_{1-6}$ fluoroalkyl, C$_{1-6}$ alkyl substituted with K, C$_{1-6}$ fluoroalkyl substituted with K, 9-fluorenylmethyl, phenyl, phenyl substituted with J, phenyl disubstituted with J, phenyl trisubstituted with J, naphthyl, naphthyl substituted with J, naphthyl disubstituted with J, naphthyl trisubstituted with J, C$_{1-6}$ alkyl with an attached phenyl group, $C_{1-6}$ alkyl with two attached phenyl groups, $C_{1-6}$ alkyl with an attached phenyl substituted with J, or $C_{1-6}$ alkyl with two attached phenyl groups substituted with J, wherein D represents $C_{1-6}$ fluoroalkyl, $C_{1-6}$ alkyl substituted with K, $C_{1-6}$ fluoroalkyl substituted with K, 9-fluorenylmethyl, phenyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group substituted with J, or $C_{1-6}$ alkyl with two attached phenyl groups substituted with J, wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl—O—CO—, $C_{1-6}$ alkyl—O—CO—NH—, or $C_{1-6}$ alkyl—S—, wherein K represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl—O—CO—, or $C_{1-6}$ alkyl—O—CO—NH, $C_{1-6}$ alkyl—S—, or tosylamino, and Y is selected from the group consisting of H, halogen, trifluoromethyl, methyl, OH and methoxy.

2. A compound of the formula:

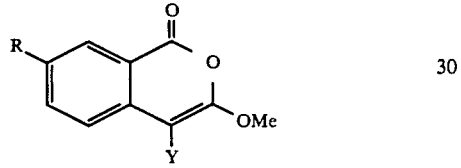

or a pharmaceutically acceptable salt thereof, wherein R is selected from the group consisting of M—AA—NH— and M—AA—O—, wherein M represents $NH_2$—CO—, $NH_2$—CS—, $NH_2$—$SO_2$—, X—NH—CO—, X—NH—CS—, X—NH—$SO_2$—, X—CO—, X—CS—, X—$SO_2$—, X—O—CO—, or X—O—CS—, wherein X represents $C_{1-6}$ alkyl, $C_{1-6}$ fluoroalkyl, $C_{1-6}$ alkyl substituted with K, $C_{1-6}$ fluoroalkyl substituted with K, 9-fluorenylmethyl, phenyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group, $C_{1-6}$ alkyl with two attached phenyl groups, $C_{1-6}$ alkyl with an attached phenyl group substituted with J, or $C_{1-6}$ alkyl with two attached phenyl groups substituted with J, wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl—O—CO—, $C_{1-6}$ alkyl—O—CO—NH—, or $C_{1-6}$ alkyl—S—, wherein K represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl—O—CO—, or $C_{1-6}$ alkyl—O—CO—NH, $C_{1-6}$ alkyl—S—, or tosylamino, Y is selected from the group consisting of H, halogen, trifluoromethyl, methyl, OH and methoxy, and wherein AA represents alanine, valine, leucine, isoleucine, methionine, phenylalanine, glycine, serine, threonine, cysteine, tyrosine, asparagine, glutamine, aspartic acid, glutamic acid, lysine, arginine, beta-alanine, norleucine, norvaline, phenylglycine, alpha-aminobutyric acid, epsilon-aminocaproic acid, citrulline, hydroxyproline, ornithine or sarcosine.

3. The compound of claim 2, wherein AA is a blocked or unblocked amino acid.

4. A compound of the formula:

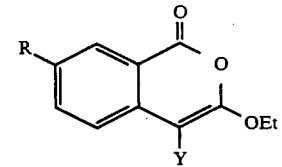

or a pharmaceutically acceptable salt thereof, wherein R is selected from the group consisting of O=C=N—, S=C=N—, M—NH—, M—O—, wherein M represents $NH_2$—CS—, $NH_2$—$SO_2$—, L—NH—CO—, X—NH—CS—, X—NH—$SO_2$—, X—CO—, X—CS—, X—$SO_2$—, X—O—CO—, or X—O—CS—, wherein L represents $C_{1-6}$ fluoroalkyl, $C_{1-6}$ alkyl substituted with K, $C_{1-6}$ fluoroalkyl substituted with K, 9-fluorenylmethyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group, $C_{1-6}$ alkyl with two attached phenyl groups, $C_{1-6}$ alkyl with an attached phenyl group substituted with J, or $C_{1-6}$ alkyl with two attached phenyl groups substituted with J, wherein X represents $C_{1-6}$ alkyl, $C_{1-6}$ fluoroalkyl, $C_{1-6}$ alkyl substituted with K, $C_{1-6}$ fluoroalkyl substituted with K, 9-fluorenylmethyl, phenyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group, $C_{1-6}$ alkyl with two attached phenyl groups, $C_{1-6}$ alkyl with an attached phenyl group substituted with J, or $C_{1-6}$ alkyl with two attached phenyl groups substituted with J, wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl—O—CO—, $C_{1-6}$ alkyl—O—CO—NH—, or $C_{1-6}$ alkyl—S—, wherein K represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl—O—CO—, or $C_{1-6}$ alkyl—O—CO—NH, $C_{1-6}$ alkyl—S—, or tosylamino, and Y is selected from the group consisting of H, halogen, trifluoromethyl, methyl, OH and methoxy.

5. A compound of the formula:

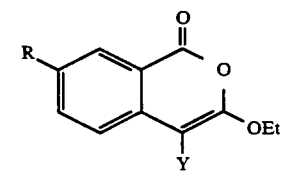

or a pharmaceutically acceptable salt thereof, wherein

R is selected from the group consisting of M—AA—NH— and M—AA—O—,
wherein M represents NH$_2$—CO—, NH$_2$—CS—, NH$_2$—SO$_2$—, X—NH—CO—, X—NH—CS—, X—NH—SO$_2$—, X—CO—, X—CS—, X—SO$_2$—, X—O—CO—, or X—O—CS—,
wherein X represents C$_{1-6}$ alkyl, C$_{1-6}$ fluoroalkyl, C$_{1-6}$ alkyl substituted with K, C$_{1-6}$ fluoroalkyl substituted with K, 9-fluorenylmethyl, phenyl, phenyl substituted with J, phenyl disubstituted with J, phenyl trisubstituted with J, naphthyl, naphthyl substituted with J, naphthyl disubstituted with J, naphthyl trisubstituted with J, C$_{1-6}$ alkyl with an attached phenyl group, C$_{1-6}$ alkyl with two attached phenyl groups, C$_{1-6}$ alkyl with an attached phenyl group substituted with J, or C$_{1-6}$ alkyl with two attached phenyl groups substituted with J,
wherein J represents halogen, COOH, OH, CN, NO$_2$, NH$_2$, C$_{1-6}$ alkyl, C$_{1-6}$ alkoxy, C$_{1-6}$ alkylamine, C$_{1-6}$ dialkylamine, C$_{1-6}$ alkyl—O—CO—, C$_{1-6}$ alkyl—O—CO—NH—, or C$_{1-6}$ alkyl—S—,
wherein K represents halogen, COOH, OH, CN, NO$_2$, NH$_2$, C$_{1-6}$ alkoxy, C$_{1-6}$ alkylamine, C$_{1-6}$ dialkylamine, C$_{1-6}$ alkyl—O—CO—, or C$_{1-6}$ alkyl—O—CO—NH, C$_{1-6}$ alkyl—S—, or tosylamino,
Y is selected from the group consisting of H, halogen, trifluoromethyl, methyl, OH and methoxy, and
wherein AA represents alanine, valine, leucine, isoleucine, methionine, phenylalanine, glycine, serine, threonine, cysteine, tyrosine, asparagine, glutamine, aspartic acid, glutamic acid, lysine, arginine, beta-alanine, norleucine, norvaline, phenylglycine, alpha-aminobutyric acid, epsilon-aminocaproic acid, citrulline, hydroxyproline, ornithine or sarcosine.

6. The compound of claim 5, wherein AA is a blocked or unblocked amino acid.

7. A compound of the formula:

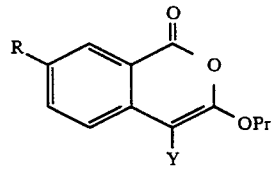

or a pharmaceutically acceptable salt thereof, wherein R is selected from the group consisting of O=C=N—, S=C=N—, M—NH—, M—O—,
wherein M represents NH$_2$—CO—, NH$_2$—CS—, NH$_2$—SO$_2$—, X—NH—CO—, X—NH—CS—, X—NH—SO$_2$—, X—CO—, X—CS—, X—SO$_2$—, X—O—CO—, X—O—CS—,
wherein X represents C$_{1-6}$ alkyl, C$_{1-6}$ fluoroalkyl, C$_{1-6}$ alkyl substituted with K, C$_{1-6}$ fluoroalkyl substituted with K, 9-fluorenylmethyl, phenyl, phenyl substituted with J, phenyl disubstituted with J, phenyl trisubstituted with J, naphthyl, naphthyl substituted with J, naphthyl disubstituted with J, naphthyl trisubstituted with J, C$_{1-6}$ alkyl with an attached phenyl group, C$_{1-6}$ alkyl with two attached phenyl groups, C$_{1-6}$ alkyl with an attached phenyl group substituted with J, or C$_{1-6}$ alkyl with two attached phenyl groups substituted with J,
wherein J represents halogen, COOH, OH, CN, NO$_2$, NH$_2$, C$_{1-6}$ alkyl, C$_{1-6}$ alkoxy, C$_{1-6}$ alkylamine, C$_{1-6}$ dialkylamine, C$_{1-6}$ alkyl—O—CO—, C$_{1-6}$ alkyl—O—CO—NH—, or C$_{1-6}$ alkyl—S—,
wherein K represents halogen, COOH, OH, CN, NO$_2$, NH$_2$, C$_{1-6}$ alkoxy, C$_{1-6}$ alkylamine, C$_{1-6}$ dialkylamine, C$_{1-6}$ alkyl—O—CO—, or C$_{1-6}$ alkyl—O—CO—NH, C$_{1-6}$ alkyl—S—, or tosylamino,
wherein K represents halogen, COOH, OH, CN, NO$_2$, NH$_2$, C$_{1-6}$ alkoxy, C$_{1-6}$ alkylamine, C$_{1-6}$ dialkylamine, C$_{1-6}$ alkyl—O—CO—, or C$_{1-6}$ alkyl—O—CO—NH, C$_{1-6}$ alkyl—S—, or tosylamino,
Y is selected from the group consisting of H, halogen, trifluoromethyl, methyl, OH and methoxy.

8. A compound of the formula:

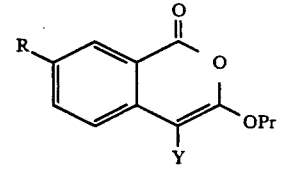

or a pharmaceutically acceptable salt thereof, wherein R is selected from the group consisting of M—AA—NH— and M—AA—O—,
wherein M represents NH$_2$—CO—, NH$_2$—CS—, NH$_2$—SO$_2$—, X—NH—CO—, X—NH—CS—, X—NH—SO$_2$—, X—CO—, X—CS—, X—SO$_2$—, X—O—CO—, X—O—CS—,
wherein X represents C$_{1-6}$ alkyl, C$_{1-6}$ fluoroalkyl, C$_{1-6}$ alkyl substituted with K, C$_{1-6}$ fluoroalkyl substituted with K, 9-fluorenylmethyl, phenyl, phenyl substituted with J, phenyl disubstituted with J, phenyl trisubstituted with J, naphthyl, naphthyl substituted with J, naphthyl disubstituted with J, naphthyl trisubstituted with J, C$_{1-6}$ alkyl with an attached phenyl group, C$_{1-6}$ alkyl with two attached phenyl groups, C$_{1-6}$ alkyl with an attached phenyl group substituted with J, or C$_{1-6}$ alkyl with two attached phenyl groups substituted with J,
wherein J represents halogen, COOH, OH, CN, NO$_2$, NH$_2$, C$_{1-6}$ alkyl, C$_{1-6}$ alkoxy, C$_{1-6}$ alkylamine, C$_{1-6}$ dialkylamine, C$_{1-6}$ alkyl—O—CO—, C$_{1-6}$ alkyl—O—CO—NH—, or C$_{1-6}$ alkyl—S—,
wherein K represents halogen, COOH, OH, CN, NO$_2$, NH$_2$, C$_{1-6}$ alkoxy, C$_{1-6}$ alkylamine, C$_{1-6}$ dialkylamine, C$_{1-6}$ alkyl—O—CO—, or C$_{1-6}$ alkyl—O—CO—NH, C$_{1-6}$ alkyl—S—, or tosylamino,
Y is selected from the group consisting of H, halogen, trifluoromethyl, methyl, OH and methoxy, and
wherein AA represents alanine, valine, leucine, isoleucine, methionine, phenylalanine, glycine, serine, threonine, cysteine, tyrosine, asparagine, glutamine, aspartic acid, glutamic acid, lysine, arginine, beta-alanine, norleucine, norvaline, phenylglycine, alpha-aminobutyric acid, epsilon-aminocaproic acid, citrulline, hydroxyproline, ornithine or sarcosine.

9. The compound of claim 8, wherein AA is a blocked or unblocked amino acid.

10. A compound of the formula:

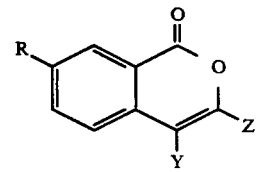

or a pharmaceutically acceptable salt thereof, wherein
Z is selected from the group consisting of $C_{1-6}$ alkoxy with a halogen attached to the alkoxy group, $C_{1-6}$ alkyl with a halogen attached to the alkyl group, $C_{1-6}$ alkoxy with an attached $C_{1-6}$ alkoxy group substituted with Q,
wherein Q represents H, or $C_{1-6}$ alkoxy,
R is selected from the group consisting of OH, $NH_2$, $NO_2$, O=C=N—, S=C=N—, M—NH—, M—O—,
wherein M represents $NH_2$—CO—, $NH_2$—CS—, $NH_2$—$SO_2$—, X—NH—CO—, X—NH—CS—, X—NH—$SO_2$—, X—CO—, X—CS—, X—$SO_2$—, X—O—CO—, or X—O—CS—,
wherein X represents $C_{1-6}$ alkyl, $C_{1-6}$ fluoroalkyl, $C_{1-6}$ alkyl substituted with K, $C_{1-6}$ fluoroalkyl substituted with K, phenyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group, $C_{1-6}$ alkyl with two attached phenyl groups, $C_{1-6}$ alkyl with an attached phenyl group substituted with J, or $C_{1-6}$ alkyl with two attached phenyl groups substituted with J,
wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl—O—CO—, $C_{1-6}$ alkyl—O—CO—NH—, or $C_{1-6}$ alkyl—S—,
wherein K represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl—O—CO—, or $C_{1-6}$ alkyl—O—CO—NH—, $C_{1-6}$ alkyl—S—, or tosylamino, and
Y is selected from the group consisting of H, halogen, trifluoromethyl, methyl, OH and methoxy.

11. A compound of the formula:

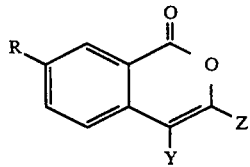

or a pharmaceutically acceptable salt thereof, wherein
Z is selected from the group consisting of $C_{1-6}$ alkoxy with a halogen attached to the alkoxy group, $C_{1-6}$ alkyl with a halogen attached to the alkyl group, $C_{1-6}$ alkoxy with an attached $C_{1-6}$ alkoxy group substituted with Q,
wherein Q represents H, or $C_{1-6}$ alkoxy,
R is selected from the group consisting of AA—NH—, M—AA—NH—, and M—AA—O—,
wherein M represents $NH_2$—CO—, $NH_2$—CS—, $NH_2$—$SO_2$—, X—NH—CO—, X—NH—CS—, X—NH—$SO_2$—, X—CO—, X—CS—, X—$SO_2$—, X—O—CO—, or X—O—CS—,
wherein X represents $C_{1-6}$ alkyl, $C_{1-6}$ fluoroalkyl, $C_{1-6}$ alkyl substituted with K, $C_{1-6}$ fluoroalkyl substituted with K, phenyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group, $C_{1-6}$ alkyl with two attached phenyl groups, $C_{1-6}$ alkyl with an attached phenyl group substituted with J, or $C_{1-6}$ alkyl with two attached phenyl groups substituted with J,
wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl—O—CO—, $C_{1-6}$ alkyl—O—CO—NH—, or $C_{1-6}$ alkyl—S—,
wherein K represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl—O—CO—, or $C_{1-6}$ alkyl—O—CO—NH—, $C_{1-6}$ alkyl—S—, or tosylamino,
Y is selected from the group consisting of H, halogen, trifluoromethyl, methyl, OH and methoxy, and
wherein AA represents alanine, valine, leucine, isoleucine, methionine, phenylalanine, glycine, serine, threonine, cysteine, tyrosine, asparagine, glutamine, aspartic acid, glutamic acid, lysine, arginine, beta-alanine, norleucine, norvaline, phenylglycine, alpha-aminobutyric acid, epsilon-aminocaproic acid, citrulline, hydroxyproline, ornithine or sarcosine.

12. The compound of claim 11, wherein AA is a blocked or unblocked amino acid.

13. The compound of claim 10, wherein
Z is selected from the group consisting of $C_{1-6}$ alkoxy with a phenyl group attached to the $C_{1-6}$ alkoxy, $C_{1-6}$ alkyl with a phenyl group attached to the $C_{1-6}$ alkyl, $C_{1-6}$ alkoxy with an attached phenyl group substituted with J, $C_{1-6}$ alkyl with an attached phenyl group substituted with J,
R is selected from the group consisting of OH, $NH_2$, $NO_2$, O=C=N—, S=C=N—, M—NH—, M—O—.

14. The compound of claim 10, wherein
Z is selected from the group consisting of $C_{1-6}$ alkoxy with a phenyl group attached to the $C_{1-6}$ alkoxy, $C_{1-6}$ alkyl with a phenyl group attached to the $C_{1-6}$ alkyl, $C_{1-6}$ alkoxy with an attached phenyl group substituted with J, $C_{1-6}$ alkyl with an attached phenyl group substituted with J,
R is selected from the group consisting of AA—NH—, M—AA—NH—, and M—AA—O—,
wherein AA represents alanine, valine, leucine, isoleucine, methionine, phenylalanine, glycine, serine, threonine, cysteine, tyrosine, asparagine, glutamine, aspartic acid, glutamic acid, lysine, arginine, beta-alanine, norleucine, norvaline, phenylglycine, alpha-aminobutyric acid, epsilon-aminocaproic acid, citrulline, hydroxyproline, ornithine or sarcosine.

15. The compound of claim 14, wherein AA is a blocked or unblocked amino acid.

* * * * *